United States Patent [19]

Elting et al.

[11] Patent Number: 5,061,790

[45] Date of Patent: Oct. 29, 1991

[54] OXIDATIVE DENATURATION OF PROTEIN ANALYTES

[75] Inventors: James J. Elting, Madison; Heinz Kolbl, West Haven, both of Conn.

[73] Assignee: Molecular Diagnostics, Inc., West Haven, Conn.

[21] Appl. No.: 377,680

[22] Filed: Jul. 10, 1989

[51] Int. Cl.[5] .................. C07K 3/00; C07K 13/00; C07K 15/00; C07K 17/00
[52] U.S. Cl. .................... 530/402; 530/403; 530/404; 530/405; 530/406; 530/408; 530/409; 530/410
[58] Field of Search ............. 530/402, 403, 404, 405, 530/406, 408, 409, 410

[56] References Cited

U.S. PATENT DOCUMENTS

| | | | |
|---|---|---|---|
| 4,033,819 | 7/1977 | Helting | 530/405 |
| 4,658,022 | 4/1987 | Knowles et al. | 436/87 |
| 4,683,136 | 7/1987 | Milich et al. | 530/403 |
| 4,713,366 | 12/1987 | Stevens | 530/326 |

Primary Examiner—Nathan M. Nutter
Attorney, Agent, or Firm—A. L. Klawitter

[57] ABSTRACT

A method for conferring or increasing the antigenicity of a disulfide-crosslinked protein by treating the protein with an oxidizing agent, such as periodate, having an oxidation potential sufficient to cleave disulfide linkages. Excess oxidizing agent is then inactivated by addition of a reducing agent. The resulting protein exhibits an increase in its ability to be bound by select antibodies, particularly monoclonal antibodies directed to linear peptide epitopes in the protein.

7 Claims, 6 Drawing Sheets

OXIDATIVE DENATURATION OF PROTEIN ANALYTES

BACKGROUND OF THE INVENTION

This invention relates to methods for binding a protein with an antibody reagent such as is performed in an immunoassay. More particularly, the invention relates to methods for denaturing a disulfide-crosslinked protein to enhance the ability of an antibody directed thereto to bind with the protein.

Immunoassays are methods for the detection or determination of substances of analytical interest (analytes) based on the binding of such substances by antibody reagents. Current technology permits the development of antibodies against a wide variety of analytes. Immunoassays are particularly useful in diagnostic medicine where analytes of clinical importance are often present at low concentrations in the presence of many structurally similar background substances.

It is now known that the antigenicity of proteins, that is, the ability of proteins to be bound by antibodies directed against the protein, in certain circumstances can critically require, or be increased by, subjecting the protein to denaturing conditions prior to contact with antibody. In certain circumstances, a desired epitope on a protein can be sterically hindered, occluded, or buried in the native three-dimensional folded structure of the protein. Denaturation can relieve the steric constraints on the epitope, thereby rendering it available or more available for antibody binding. Thus, denaturation can be significant in the development of an immunoassay where available antibody reagents do not bind with the native form of the protein or where binding is too weak for the concentration of protein to be detected.

For example, U.S. Pat. No. 4,658,022 describes a general principle that the binding of antibodies directed to linear peptide epitopes in proteins can be obtained or enhanced by denaturation of the protein. This has been particularly applied in the case of proteins in which the epitope that characterizes it relative to other proteins that are present in a test sample is sterically hindered in the native form of the protein. An example is the glycated form of hemoglobin known as hemoglobin A1c. The patent describes a wide variety of means for denaturing a protein for the purposes of creating or enhancing antigenicity, including heating, sonication, treatment at high or low pH, and treatment with chemical denaturants and chaotropic agents such as guanidine, urea, and detergents. It is further reported that inclusion of reagents such as mercaptoethanol or dithiothreitol which reduce disulfide bonds can be effective promoters of the denaturation process.

It is known that the structure of many proteins includes disulfide linkages between adjacent peptide chains. Such linkages are important in defining the native three-dimensional structure of such proteins. Studies of protein structure often involve the cleavage of disulfide linkages. Such cleavage is required for complete denaturation of the protein and is generally accomplished by exposure to reducing agents (e.g., mercaptoethanol or dithiothreitol) followed by the addition of capping agents (e.g., iodoacetic acid or iodoacetamide).

SUMMARY OF THE INVENTION

It has now been found that antigenicity of disulfide crosslinked proteins can be conferred or increased by cleavage of disulfide linkages and that such cleavage can be advantageously accomplished by treating the protein with an oxidizing agent of appropriate oxidation potential and thereafter inactivating remaining oxidizing agent by addition of a suitable reducing agent. This oxidative denaturation has been found to expose, and increase the exposure of, epitopes, particularly linear peptide epitopes, in disulfide crosslinked proteins. The oxidative method does not require the use of high concentrations of chaotropic agents or the use of sulfhydryl capping reagents, both of which can be deleterious to antibody binding. Treatment with the oxidizing agent followed by reducing agent produces a denatured protein mixture which is compatible with antibody binding to exposed epitopes in the protein. Additionally, the denaturation is rapid and the denaturing reagents are generally inexpensive.

DESCRIPTION OF THE PREFERRED EMBODIMENTS

It will be understood that disulfide linkages in proteins comprise three covalent bonds, a sulfur:sulfur bond between two carbon:sulfur bonds. For the purposes of the present invention, it is not considered significant which of these three individual bonds are broken in order to obtain cleavage of the linkage. Cleavage of any of such bonds will provide the desired denaturation effect.

It will be evident that a wide variety of oxidizing agents and conditions will be suitable for the purpose of cleaving the disulfide linkages. Selection of a particular oxidant and oxidizing conditions will be made in accordance with the requirements and tolerances of the particular protein involved and the binding properties of the anti-protein antibody to be bound to the protein. In general, the oxidation potential of the oxidizing agent will need to be sufficiently high to produce significant cleavage. In experiments thus far, oxidizing agents having an oxidation potential above about 1.3 volts have proven to be effective. Significantly increasing the oxidizing power of the cleaving agent can result in undesirable side reactions and chemical modification of the protein. With these considerations in mind, the ordinary skilled worker can design or determine suitable oxidation conditions for a given situation.

Representative examples of oxidizing agents that can be used in the present invention, without limitation, are periodate, ($IO_4^-$), peroxodisulfate ($S_2O_8^=$), hypochlorite ($OCl^-$), chromate ($CrO_4$), and perchlorate $ClO_4^-$). Periodate has exhibited particularly useful denaturation effects, particularly when present at concentrations in the denaturing mixture of between about 0.001 and about 0.2 molar (M), and preferably between about 0.01 and 0.05M. The countercation in the above oxidizing agents is generally not critical; one will normally select from potassium, sodium, lithium, calcium, magnesium, barium, and ammonium. The addition of metal ions can enhance oxidation and/or lower the temperature requirements, such as the addition of appropriate ionic forms of cobalt, vanadium, iron, manganese, copper, chromium, tin, ruthenium, lead, cerium, nickel, and neptunium.

The denaturation effect will also generally be dependent upon other parameters such as temperature, pH, incubation time, and the like. Normally, the oxidation reaction will be conveniently performed at temperatures between room temperature and about 70° C. e.g., between about 20° C. and about 70° C. Denaturation at room temperature will normally be preferred, however, in some situations it will be desirable or necessary to oxidize at slightly elevated temperatures, e.g., between about 35° C. and about 70° C.

Depending upon the oxidizing agent involved, the pH of the denaturing medium can affect the oxidation potential, and therefore, the effectiveness of the oxidation reaction. In more general terms, the pH can vary within a wide range, taking normal precautions not to cause chemical modification of the protein molecule. Accordingly, the pH of the denaturing reaction can be between about 3 and about 11, although more usually the pH will be controlled between about 4 and about 7.

While the other parameters of the oxidation reaction will usually be optimized in order that the incubation time can be minimized, it would be expected that the reaction could be allowed to proceed for anywhere from a few seconds, e.g., 0.1 minute, up to several hours. In analytical situations, conditions will normally be optimized for incubation times of between about 30 seconds and about 10 minutes.

As with the oxidizing agent, the reducing agent used to quench remaining oxidant after completion of the desired denaturation can be selected from a wide range of materials. Selection will depend on the reduction potential necessary to effectively neutralize the oxidizing power of the oxidant and the need to avoid interfering side reactions and modification of the protein. Representative reducing agents for this purpose are, without limitation, thiosulfate ($S_2O_3^=$), dithionite ($S_2O_4^=$), dithiothreitol, dithioerythritol, and mercaptoethanol.

As used herein, the term antibody or antibody reagent is intended to encompass any material, however obtained, which comprises an antibody combining site. Thus, included in the intended meaning of the term are whole antibodies as well as appropriate fragments or polyfunctionalized forms thereof. When in the form of whole antibody, it can belong to any of the classes and subclasses of known immunoglobulins, e.g., IgG, IgM, and so forth. Any fragment of any such immunoglobulin which retains the antibody combining site can also be employed, for instance, the fragments of IgG conventionally known as Fab, Fab', and F(ab')$_2$. In addition, aggregates, polymers, derivatives, conjugates, and hybrids of immunoglobulins or their fragments can also be used where appropriate.

The immunoglobulin source of the antibody reagent can be derived by any available technique such as conventional antiserum production or monoclonal techniques. At the appropriate point in the generation of antibody, a host animal will be immunized with a material (conventionally referred to as an immunogen) in order to stimulate the production of desired antibodies by the immune system of the host. One skilled in the art will choose an appropriate immunogen for the binding properties of the antibody desired. Since the present invention relates to a situation where the epitope on the protein to which the antibody reagent is directed is unavailable or of limited availability in the native protein, immunogens will normally have been of a structure that displays the epitope in a non-native form. This is particularly applicable where the epitope is a linear peptide epitope, that is, the antibody is directed to a region on the protein consisting of a linear sequence of amino acid residues.

For example, the immunogen can be a denatured form of the whole protein, or of a digested or synthesized fragment thereof (in the latter cases, the fragments may be chemically attached to a conventional immunogenic carrier material). Further, the immunogen can be a synthetic peptide immunogen, that is, a conjugate of a synthetically prepared peptide, comprising, for example, at least about four amino acid residues, chemically coupled to a heterologous immunogenic carrier (e.g., bovine serum albumin, keyhole lympet hemocyanin, or the like). The use of synthetic peptide immunogens is intended to direct the immune response to a linear peptide epitope. Where such linear epitope in a native disulfide-crosslinked protein is found to be inaccessible, or of limited access, to the antibody that is stimulated, the present invention provides a means for exposing the epitope, or for increasing its exposure, through denaturation.

The present invention is contemplated to be applicable to essentially any protein containing one or more disulfide bridges. It will be apparent that the present oxidative denaturation will not successfully confer or increase the antigenicity of every disulfide-crosslinked protein relative to any antibody directed thereto since such will depend upon the particular structure and folding of the protein and the location of the epitope within the three-dimensional native structure of the protein. However, one skilled in the art will quite readily be able to determine the usefulness of the present approach in those instances where antibodies are suspected to have been raised against a sterically hindered or hidden epitope in a disulfide-crosslinked protein.

Accordingly, the present invention will be potentially applicable to essentially any desired protein, including those having lower molecular weights, e.g., 5000 daltons or less (as used herein, the term protein shall include those compounds which might in other contexts be referred to as polypeptides because of their molecular weight), as well as those having molecular weights of several hundred thousand or more. Representative classes of proteins include protamines, mucoproteins, glycoproteins, globulins, albumins, phophoproteins, histones, lipoproteins, chromoproteins, and nucleoproteins.

The present invention is particularly applicable to immunoassays and reagent systems for the specific determination of particular disulfide-crosslinked protein analytes. The present invention will afford the opportunity to find new and useful linear peptide epitopes and to increase the accessibility of such epitopes in disulfide-crosslinked proteins of interest. The present method provides an approach for designing an antibody reagent and establishing binding conditions to enable successful or improved specific detection of the protein in cases where the characterizing epitope is inaccessible or only limitedly accessible to antibody binding in the native protein. Another application of this invention will be in finding epitopes in disulfide-crosslinked proteins which are more specific and/or having higher binding affinities than those available for antibody formation and binding on the normally exposed portions of the protein. By immunizing a desired host animal with a suitably denatured form of a protein or a fragment thereof, one can then examine the resulting immune response for antibodies exhibiting the desired increased specificity and/or avidity. An extension of this application is in the specific detection of cellular analytes such as blood cells, microorganisms including bacteria and viruses, and the like. In cases where it is desirable to improve the specificity of detection over that afforded by antibody binding to surface protein antigens, one can examine the internal epitopes by denaturing the surface proteins and/or proteins within the cell to look for improved antibody response.

The immunoassay determination of a protein analyte using the present invention can follow essentially any conventional technique. Such include the more classical techniques such as immunodiffusion, immunoelectrophoresis, agglutination techniques, and complement fixation, as well as more current techniques involving the use of specifically detectable labels such as radioimmunoassay and nonradioisotopic methods. The performance of an immunoassay for a protein analyte employing the present invention involves the essential steps of treating the aqueous test sample involved to effectively denature a significant amount of any such protein therein to expose the desired epitope, contacting the denatured sample with the antibody reagent, and determining binding of the antibody reagent to such protein. The determination step will of course vary according to the basic immunoassay technique involved. A common technique for making this determination involves the use of a labeled reagent which interacts with either the analyte or antibody reagent and is employed in a manner to indicate the formation of immune complex between analyte and the antibody reagent or to compete with such formation.

The latter techniques can be practiced in a wide variety of formats such as the competitive binding format in which a labeled reagent is made to compete with the protein analyte for binding to the antibody reagent. The amount of labeled reagent bound to the antibody reagent, or the free-species, consisting of the labeled reagent which is not so bound, is measured appropriately and can be functionally related to the amount of protein analyte in the sample. Where the antibody reagent of the present invention is directed to a linear epitope in the protein analyte, the labeled reagent can be a labeled form of the denatured protein or a denatured fragment thereof, or, as would be preferred, a labeled form of a peptide residue comprising the linear epitope sequence of amino acids. The latter, preferred reagent can be prepared by available synthetic peptide methods and apparatus and does not require isolation, purification, and denaturation of the protein molecule itself.

Another useful immunoassay technique for the detection of protein analytes is that known as the sandwich technique. In this method, one would employ two antibody reagents, one of which would be labeled and the other would be adapted to effect separation of ultimately labeled first antibody reagent bound to the protein analyte from that which is unbound. The unlabeled second antibody reagent typically is in an immobilized or immobilizable form as is known in the art.

In radioimmunoassays, the free-species and bound-species must be physically distinguished or separated in order to measure the label since the signal generated by the label is qualitatively the same in both species. Such a technique is known in the art as heterogeneous because of the phase separation requirement. Other heterogeneous immunoassay techniques are known including enzyme-labeled immunoassays, sometimes referred to as ELISA techniques (see U.S. Pat. No. 3,654,090), and fluorescent immunoassays (see U.S. Pat. Nos. 4,201,763: 4,133,639 and 3,992,631). Immunoassay techniques known as homogeneous techniques will also be applicable to the present invention.

The present invention will now be illustrated, but is not intended to be limited, by the following examples.

EXAMPLES

A. Antigenicity of Carcinoembryonic Antigen (CEA)—Effect of Oxidation with Periodate In this Example, the detectability of CEA by sandwich immunoassay was compared for native CEA, CEA that had been denatured by oxidation with periodate in accordance with the present invention, and CEA that had been denatured by the methods of the prior art (reduction followed by alkylation).

Oxidized CEA—6 microliters ($\mu$L) of a solution containing 1 milligram/milliliter (mg/mL) of CEA (Scripps Laboratories, San Diego, Calif., USA) were dissolved in 294 $\mu$L of 0.02M sodium periodate ($NaIO_4$) in phosphate-buffered saline at pH 5 (PBST $-$ 10 mM sodium phosphate, 0.15M sodium chloride, 0.05% Tween $-$20 and 0.01% thimerosal, with pH adjusted by addition of sodium hydroxide) and heated in a sealed test tube to 70° C. for 5 minutes. The solution was cooled in an ice bath, 300 $\mu$L of 0.03M sodium thiosulfate ($Na_2S_2O_3$) in PBST (pH 5) added, and the solution mixed by vortex. [Oxidized CEA preparations are referred to herein by the abbreviation "OCEA". Native CEA is referred to as "CEA".]

Reduced and Alkylated CEA—Method of Brew et al., J. Biol. Chem. 245:457)1970). [Reduced and alkylated CEA preparations are referred to herein by the abbreviation "RACEA".]

Sandwich Immunoassay—The selected antigen preparations are respectively serially diluted 1:3 with PBST (pH 5) ten (10) times.

A two-antibody microtiter plate sandwich immunoassay was performed according to standard procedures (Harlow, E. and Lane, D., Antibodies: A Laboratory Manual, Cold Spring Harbor, 1988). The microtiter plate was washed 5 times with PBST on a plate washer between each of the following steps. A mouse anti-CEA monoclonal antibody was adsorbed to the wells of a microtiter plate as capture antibody. Excess binding sites were blocked with a 1% solution of bovine serum albumin (BSA) in PBST. After the antigen addition (100 $\mu$L/well of the appropriate dilution), rabbit polyclonal anti-CEA antibody was added as the detection antibody. Detection of the rabbit antibody was accomplished by addition of 100 $\mu$L/well of a goat anti-(rabbit Ig)-(horse radish peroxidase (HRP) conjugate diluted in PBST containing 1% BSA (pH 8.2). The assay was developed by addition of a substrate (tetramethylbenzidine/hydrogen peroxide) and quantitated by reading the optical density at 450 nanometers (nm).

Figure 1:
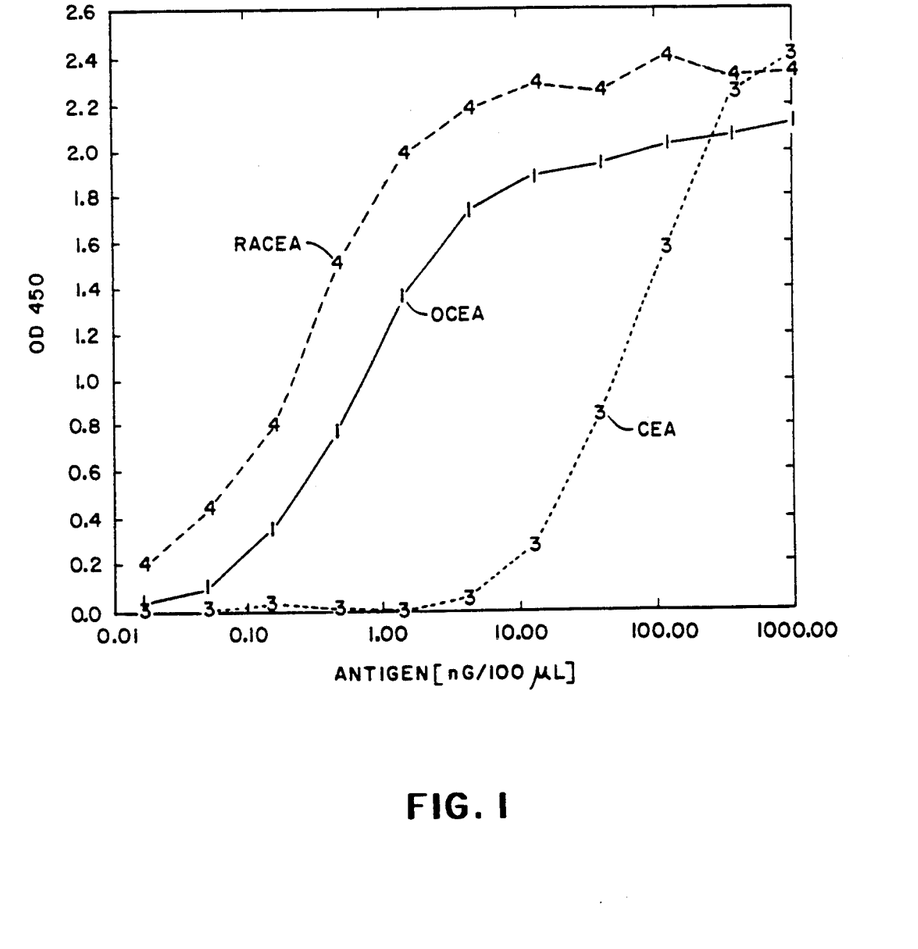
FIG. 1 is a graph showing the effect of periodate on the antigenicity of the protein antigen CEA.

Results—The above immunoassay was performed on a dilution series of CEA, OCEA, and RACEA. The results are shown in the graph of FIG. 1.

B. Antigenicity of Carcinoembryonic Antigen (CEA)—Effect of Oxidation with Peroxodisulfate The oxidation of CEA was repeated using peroxodisulfate as the oxidant.

Figure 2:
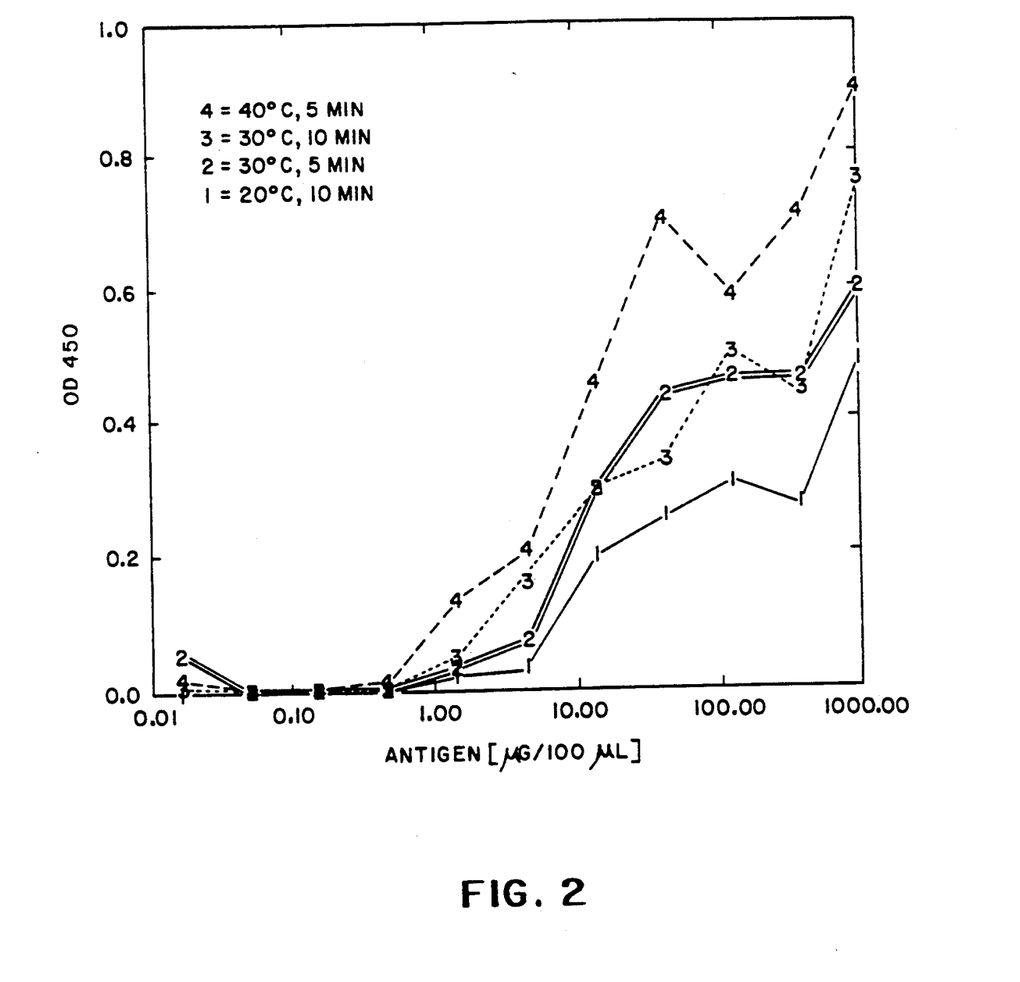
FIG. 2 is a graph showing the effect of peroxodisulfate on the antigenicity of CEA.

Oxidized CEA—23.81 μL of a solution containing 0.84 mg/mL of CEA were dissolved in 976.2 μL of 0.02M ammonium peroxodisulfate ($NH_4S_2O_8$) in PBST (pH 5). The solution was divided into four portions of 250 μL each and heated in sealed test tubes to the respective temperatures referred to in FIG. 2 for 5-10 minutes. The solutions were then cooled in an ice bath, 250 μL of 0.03M sodium thiosulfate in PBST (pH 5) was added, and the solutions mixed by vortex.

Immunoassay—Same as in Example A above.
Results—Shown in the graph of FIG. 2.

C. Antigenicity of Carcinoembryonic Antigen (CEA)—Effect of Oxidation with Hypochlorite The oxidation of CEA was repeated using hypochlorite as the oxidant.

Oxidized CEA—6 μL of a solution containing 1 mg/mL of CEA were dissolved in 294 μL of 0.002M sodium hypochlorite (NaOCl) in PBST (pH 5) and kept in a test tube at room temperature (22° C.) for 5 minutes. Then, 300 μL of 0.3M sodium thiosulfate in PBST (pH 5) was added and the solution mixed by vortex.

Figure 3:
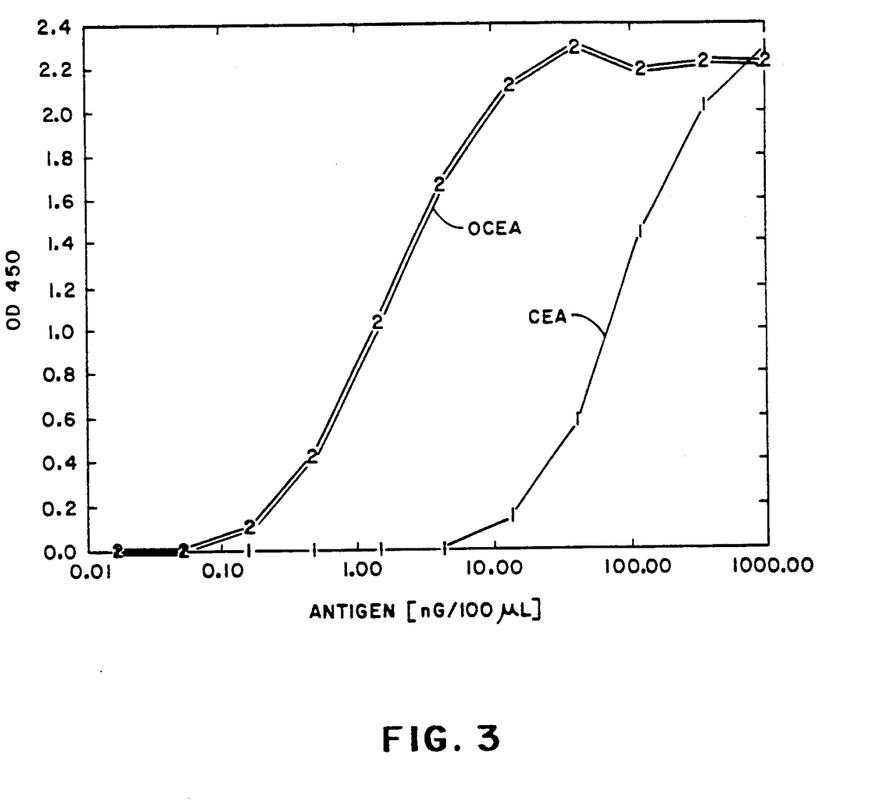
FIG. 3 is a graph showing the effect of hypochlorite on the antigenicity of CEA.

Immunoassay—Same as in Example A above.
Results—The immunoassay was performed on a dilution series of CEA and OCEA. The results are shown in the graph of FIG. 3.

D. Effect of pH

Figure 4:
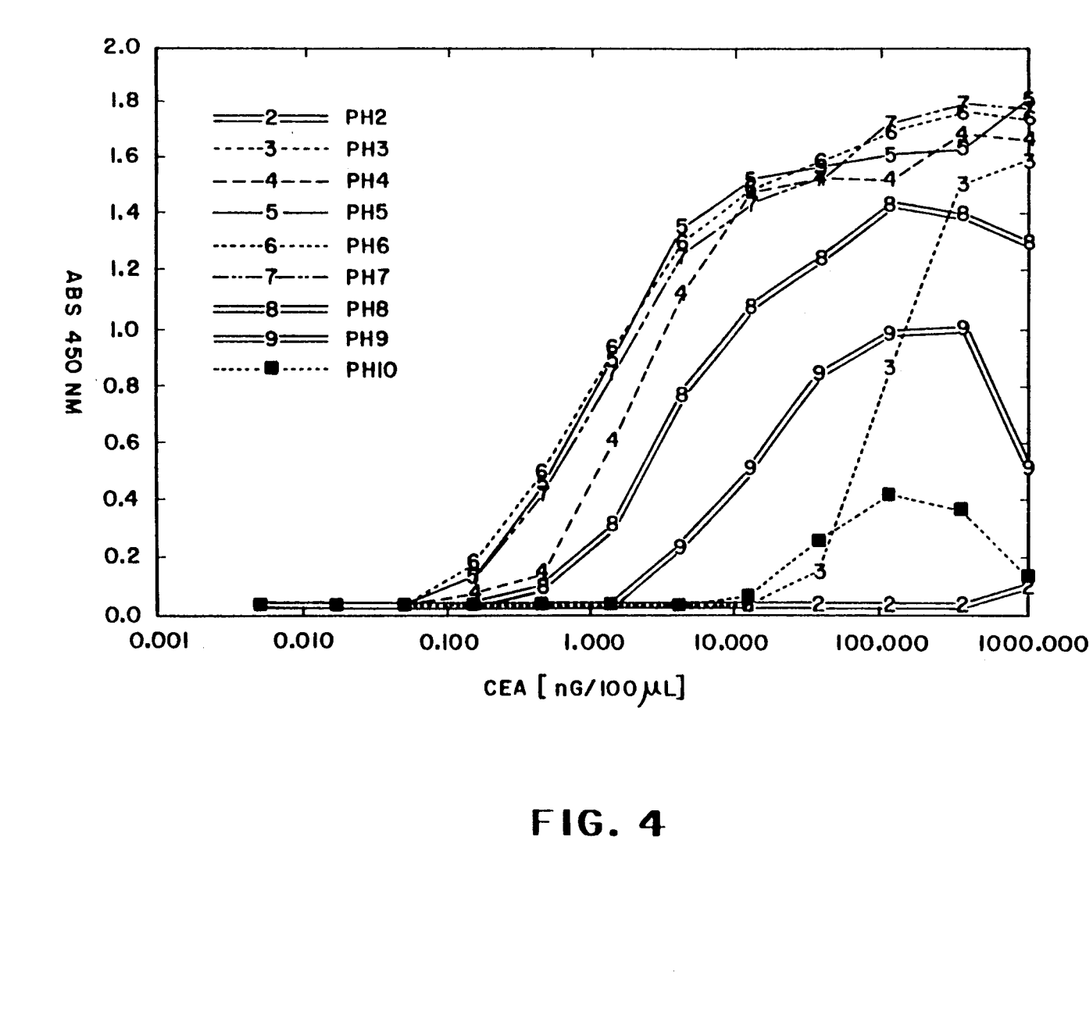
FIG. 4 is a graph showing the effect of pH on the oxidation process of the present invention.

Preparation of test samples—6 μL of a solution containing 1 mg/mL of CEA was dissolved in 294 μL of 0.02M sodium periodate in PBST at the respective pHs shown in FIG. 4. The solutions were heated in sealed test tubes to 70° C. for 5 minutes, then cooled in an ice bath. Then, 300 μL of 0.03M sodium thiosulfate in PBST at the same pH as the respective oxidation reaction were added and the solutions mixed by vortex. Any precipitation of inorganic material at any stage of the procedure was ignored. Serial dilutions were performed at the same pH for each set of test samples.

Immunoassay—Same as in Example A above.
Results—Shown in the graph of FIG. 4.

E. Effect of temperature

Figure 5:
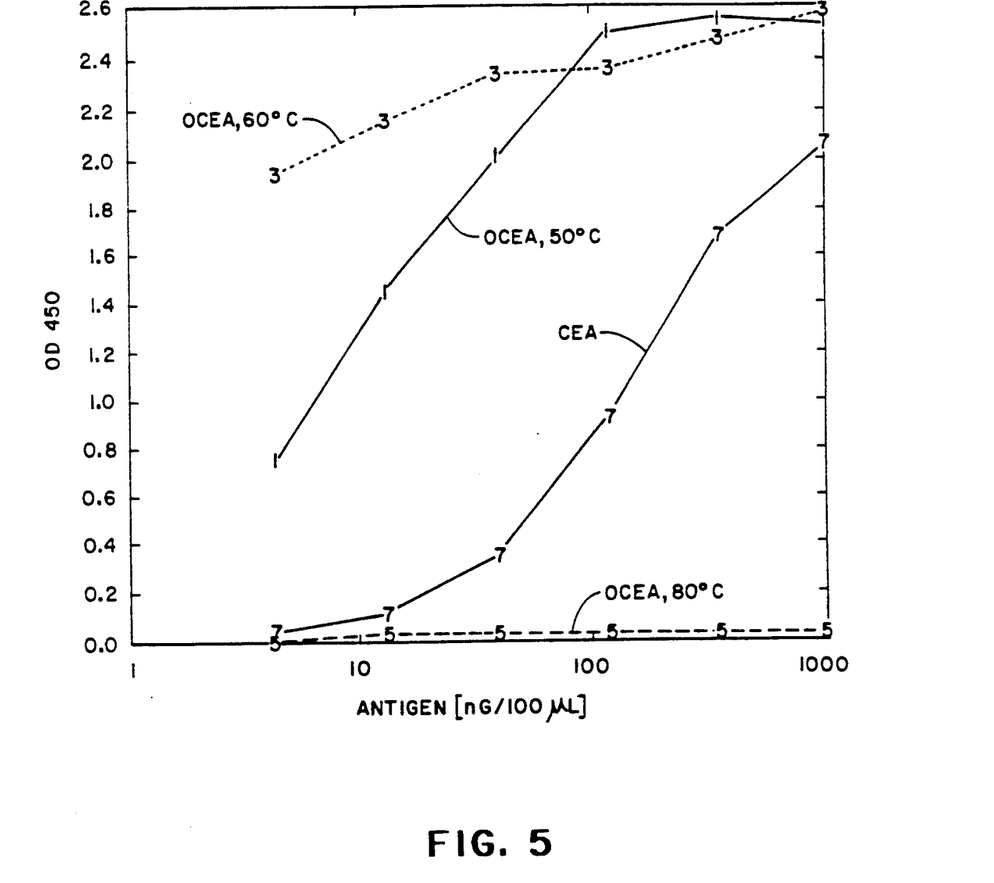
FIG. 5 is a graph showing the effect of temperature on the oxidation process of the present invention.

Preparation of test samples—18.75 μL of a solution containing 0.8 mg/mL of CEA were dissolved in 731.2 μL of 0.02M sodium periodate in PBST (pH 5). This solution was divided into three portions of 250 μL each. The test tubes were sealed and heated to the respective temperature shown in FIG. 5 for 5 minutes. The solutions were then cooled in an ice bath, 300 μL of 0.03M sodium thiosulfate in PBST (pH 5) were added to each, and the test samples mixed by vortex.

Immunoassay—Same as in Example A above.
Results—Shown in the graph of FIG. 5.

F. Comparison with Attempted Guanidine Denaturation

Figure 6:
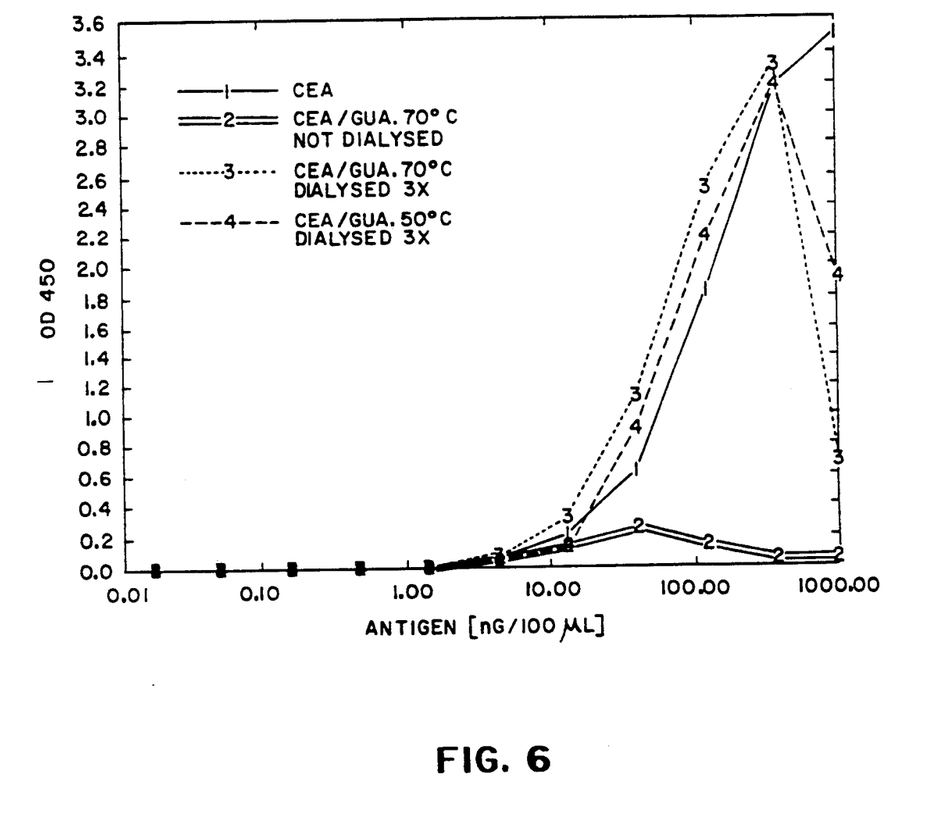
FIG. 6 is a graph showing the results of an attempted denaturation of CEA with guanidine hydrochloride without disulfide cleavage.

Preparation of test samples—26.2 μL of a solution containing 0.61 mg/mL of CEA were dissolved in 1.57 mL of a 3M guanidine hydrochloride solution in PBST (pH 5). Three 500 μL samples of this solution were placed in separate test tubes which were then sealed and heated to the respective temperatures shown in FIG. 6 for 5 minutes. The solutions were cooled in an ice bath. One of the 70° C. samples was used directly in the immunoassay. The other two were dialyzed against PBST using Amicon concentrator tubes (membrane exclusion size of 30,000 daltons, concentrating to 50 μL, rediluting to 1 mL, and centrifuging at 5000 xg). This process was repeated three times.

Immunoassay—Same as in Example A above.
Results—Shown in the graph of FIG. 6. The flat response given by the undialyzed sample is believed to be due to denaturation of the immunoassay antibody reagents.

The present invention has been particularly described and exemplified above. Clearly, many other variations and modifications of the invention can be made without departing from the spirit and scope thereof.

What is claimed is:

1. A method for conferring or increasing the antigenicity of a protein containing disulfide crosslinkages, comprising the steps of treating the protein with an oxidizing agent having an oxidation potential sufficient to cleave disulfide linkages in proteins and under conditions favorable to the cleavage of said disulfide linkages, and thereafter contacting the resulting mixture with a sufficient amount of a reducing agent to react with and inactivate remaining oxidizing agent.

2. The method of claim 1 wherein the oxidizing agent has an oxidation potential of at least about 1.3 volts.

3. The method of claim 1 wherein the oxidizing agent is selected from periodate, peroxodisulfate, hypochlorite, chromate, permanganate, and perchlorate.

4. The method of claim 1 wherein the oxidizing agent is periodate.

5. The method of claim 1 wherein the reducing agent is selected from thiosulfate, dithionite, dithiothreitol, dithioerythritol, and mercaptoethanol.

6. The method of claim 1 wherein the oxidation step is performed at a temperature of between about 20° C. and about 70° C.

7. The method of claim 1 wherein said resulting mixture is contacted with said reducing agent between about 30 seconds and about 10 minutes after treatment with said oxidizing agent.

* * * * *